United States Patent [19]

Coupek et al.

[11] 4,079,021

[45] Mar. 14, 1978

[54] POLYMERIC CARRIER FOR A CONTROLLED SYNTHESIS OF PEPTIDES

[75] Inventors: Jiri Coupek, Prague; Vladimir Gut, Uhrineves, both of Czechoslovakia

[73] Assignee: Ceskoslovenska akademie ved, Prague, Czechoslovakia

[21] Appl. No.: 549,830

[22] Filed: Feb. 13, 1975

Related U.S. Application Data

[62] Division of Ser. No. 413,390, Nov. 6, 1973, Pat. No. 3,925,267.

[30] Foreign Application Priority Data

Nov. 6, 1972 Czechoslovakia .................. 7475/72

[51] Int. Cl.² ............................. C08J 9/00; C08J 9/22
[52] U.S. Cl. .............................. 260/2.5 R; 260/2.5 B; 526/16
[58] Field of Search ................ 260/67 A, 73 L, 80.73, 260/80.81, 2.5 R, 72, 72.5, 17.4 SB, 2.5 B, 2.5 EP, 2.5 H, 2.5 HB, 823, 827, 836, 6; 526/16

[56] References Cited

U.S. PATENT DOCUMENTS

| | | |
|---|---|---|
| 3,575,946 | 4/1971 | Chromocek et al. ........... 260/86.1 E |
| 3,663,467 | 5/1972 | Albright ............................. 260/2.5 B |
| 3,699,089 | 10/1972 | Wichterle ....................... 260/86.1 E |

*Primary Examiner*—Allan Lieberman

[57] ABSTRACT

An acrylic polymer suitable for use as carrier in the controlled synthesis of polypeptides is provided. The polymer comprises the condensation product of a monomer selected from the group consisting of hydroxyalkyl acrylates and hydroxyalkyl methacrylates, a polyfunctional cross-linking monomer selected from the group consisting of alkylene diacrylates, alkylene dimethacrylates, polyacrylates and polymethacrylates of polyalochols, alkylene bisacrylamides and divinylbenzene, and an aromatic ring-containing compound selected from the group consisting of aromatic acids and their anhydrides and chlorides, aromatic isocyanates, halogenophenylsilanes, and aromatic epoxy compounds. The condensate has its aromatic rings chlormethylated. The first monomer and the polyfunctional cross-linking monomer are copolymerized and the resultant copolymer is condensed with said compounds which contain an aromatic ring.

1 Claim, No Drawings

POLYMERIC CARRIER FOR A CONTROLLED SYNTHESIS OF PEPTIDES

This is a divisional application of Ser. No. 413,390, filed Nov. 6, 1973 and now U.S. Pat. No. 3,925,267.

The invention relates to a new polymeric carrier, the method in its preparation and its application in a controlled synthesis of polypeptides.

Biologically active polypeptides may be formed by a step-wise condensation of definite aminoacids in a precisely defined sequence. The classic preparation of such compounds by condensation in solution requires the complex and expensive isolation of reaction products after every reaction step and their characterization. However, this procedure is experimentally unfeasible for peptides with longer chains. Merrifield (P. B. Merrifield; J. Am. Chem. Soc., 85, 2149 (1963)) described a method for overcoming the complications inhering in sequential stepwise condensation of aminoacids. This method consists of three stages — linking of the first aminoacid to a solid polymer carrier by covalent bond, sequential stepwise reaction of further aminoacids to form the peptide chain, and the eventual cleavage of the formed chain from the carrier and its isolation without damage.

If the growing peptide chain is covalently bound to the solid carrier during the whole sequence of stepwise condensation reactions, separation of products from unreacted agents and products of side reactions is made easy in each reaction step. Complicated isolation operations, which are necessary in the solution process, are reduced to elution or decanting of particles of the solid carrier with anchored growing polypeptide. This procedure simplified the synthesis significantly, considerably shortened the time of synthesis and made its automation possible.

A highly crosslinked copolymer of styrene with divinylbenzene, which is activated for reaction with the first aminoacid, is usually used as the carrier for polypeptide synthesis. This material has two substantial disadvantages limiting its general application. This is, in the first place, the physical structure of the copolymer, which is a xerogel and exhibits therefore a considerable dependence of mechanical properties on the polymer network density. The condensation reactions of aminoacids take place inside the physically homogeneous gel matter and the network density forms a natural limit for the molecular weight of synthesized polypeptide. Diffusion coefficients of reaction components, which have to be brought to the reaction site at the growing polypeptide chain, as well as those of reaction products, which have to be washed out after completion of the reaction, are substantially lower in the homogeneous xerogel than in solution. This fact may cause slower establishing of equilibrium in condensation reactions, negatively influence the final degree of conversion in individual reaction steps and, eventually, render more difficult and longer the washing of the material after the elementary condensation reaction. Another disadvantage of the styrene gel follows also from its homogeneously crosslinked structure; namely, it can be used only in solvents swelling the copolymer. Because these are exclusively organic solvents often of low polarity, the choice of reaction possibilities for aminoacid condensation is automatically limited. Application of aqueous reaction systems is impossible. Sorption interactions of some aminoacids with the nonpolar gel carrier may be expected in the non-aqueous medium, which fact can further render their removal after completion of the condensation step more difficult. All these facts result in a non-quantitative course of the individual reaction steps in linking aminoacids and, consequently, some aminoacids are missing in the resulting reaction product after its splitting from the carrier. This can very unfavorably affect the biological efficiency of the product.

The polymeric carrier according to this invention consists of a hydrophilic gel, which contains besides hydrophilic functional groups also aromatic rings and wherein the primary carrier is further activated by chloromethylation by reaction with formaldehyde and hydrogen chloride. The gel is formed from molecules of hydroxyalkyl acrylates, hydroxyalkyl methacrylates, aminoalkyl acrylates, aminoalkyl methacrylates, acrylamides or methacrylamides linked with a crosslinking monomer of acrylate or methacrylate type and with the third or even further monomer containing aromatic rings in its molecule, which can be activated by chloromethylation. The crosslinking comonomers of acrylate or methacrylate type may be alkylene diacrylates, alkylene dimethacrylates, acrylates or methacrylates of polyalcohols, dihydroxy- or polyhydroxyethers or alcoholic sugars, bisacrylamides or divinylbenzene. The object of this invention is further a method for preparation of a gel carrier, which does not possess the negative properties of polystyrene homogeneous gels generally used till now, and application of this gel in controlled synthesis of polypeptides. The carriers are prepared, according to this invention, by a suspension heterogeneous copolymerization of hydrophilic acrylate or methacrylate monomers with the crosslinking comonomer in the presence of a third comonomer containing an aromatic ring in the molecule, as for example phenyl acrylate, phenyl methacrylate, acrylanilide, methacrylanilide, phenylethyl acrylate or methacrylate, styrene and others. Materials with similar properties may be formed also in a subsequent modification of macroporous suspension copolymers prepared according to Czechoslovak Pat. No. 150,819 corresponding to U.S. patent application 281,288 by compounds containing the aromatic ring and forming condensation compounds with the pendent hydroxyl group of the polymer, as for example by aromatic acids, their chlorides or anhydrides, aromatic isocyanates, halogenophenylsilanes, or aromatic epoxy compounds. Finally, the primary carriers can be prepared by polymerization reactions protected by the Czechoslovak Pat. No. 166,317 (patent application PV No. 5741-72) corresponding to British Pat. No. 1,409,967, followed by diazotization of the resulting polymers and coupling with a passive aromatic component. All these copolymers have to be able to undergo chloromethylation to be activated for the reaction with the first aminoacid.

The gels with macroporous structure are formed in the process of heterogeneous suspension copolymerization and are noted for the high mechanical strength and hydrolytic stability. Their specific surface area ranges between 5 and 500 m$^2$ per gram of the copolymer and they may be prepared in a form of globular particles of uniform size. During the activation, only that portion of the aromatic rings reacts, which is exposed to the action of formaldehyde and hydrogen chloride on the surface of copolymer. When the material has a large specific surface area, its capacity is high enough in comparison with homogeneous materials. Then the synthesis of peptide takes place on the solid surface of the copolymer, which does not swell or swells only slightly due to its properties of aerogel and therefore permits the use of arbitrary polar or nonpolar organic solvent as the reaction medium. All complications connected with the slow establishing of reaction equilibria and transport of products from the reaction site, both controlled by diffusion in the gel, are also taken away.

The object of the invention is illustrated in the following examples, without, however, limiting the scope of the invention.

EXAMPLE 1

A macroporous hydrophilic copolymer was prepared by the heterogeneous suspension copolymerization of 20 weight parts of methacrylanilide, 40 wt. parts of 2-hydroxyethyl methacrylate and 40 wt. parts of ethylene dimethacrylate in the presence of inert solvents as is taught in Czechoslovak Patent Application PV No. 7919-70, to initiate the copolymerization, radical initiators soluble in the monomeric phase and insoluble in water are used, e.g., aliphatic azo compounds, diacyl peroxides, etc. The reaction temperature must be maintained constant and depends on the initiator used. In the case of azo bis-isobutyronitrile, a reaction temperature of 70 $\pm 1°$ C. is suitable; in the case of dibenzoyl peroxide, a reaction temperature of 60° C. is suitable. The water soluble polymers commonly used as protective colloids serve as the suspension stabilizers; e.g., polyvinyl pyrrolidone, poly(vinyl alcohol), starch, etc. After the conversion of 100% has been reached, the suspension is separated from the suspension medium by filtration and freed from organic solvents used as the inert component (e.g., cyclohexanol, lauryl alcohol, n-octyl alcohol) for controlling the pore size distribution by a steam distillation or extraction with low-boiling solvents. The suspension stabilizer and the other water soluble components of the system are removed by repeated washing with water. The copolymeric materials obtained are dried. This gel consisting of (2 parts by weight, 24 parts by weight of zinc (II) chloride and 12 parts by weight of concentrated hydrochloric acid were mixed with 10 parts by weight of aqueous formaldehyde solution (38%). The suspension was heated to 50° C and a steam of gaseous hydrogen chloride was led through it for 5 hours. The gel was then filtered, washed with 100 wt. parts of water and 100 wt. parts of methanol and dried in vacuum over $P_2O_5$ and NaOH for 12 hours. An analytical determination of chlorine showed 5.92% Cl.

The copolymer activated by chloromethylation (2 wt. parts) was suspended in a solution of 0.456 wt. part of o-nitrobenzenesulphenylglycine and 0.25 wt. parts of triethylamine in 8 parts of dimethylformamide and stirred at 25° C for 120 hours. The suspension was then diluted with 50 wt. parts of dimethylformamide and the gel was decanted, washed gradually with methanol, water, methanol, and dichloromethane and then dried in vacuum. After hydrolysis, 0.25 mmole of glycine per gram of the gel was determined by an aminoacid analysis.

One wt. part of the gel with bound o-nitrobenzenesulphenylglycine was washed with 50 wt. parts of C.1 M HCl in the methanol - dichloromethane mixture (1 : 1) on a glass filter during 15 min and then with pure dichloromethane. The quantitative cleavage of the protecting o-nitrobenzene-sulphenyl groups (0.25 mmole/g) was proved by measuring the optical density of filtrate at 384 nm. The aminoacid was released from its salt by elution with a solution of 1.2 wt. parts of triethylamine in 10 wt. parts of dichloromethane and the gel was then washed with pure dichloromethane. The gel was then suspended in 10 wt. parts of dichloromethane, 0.12 wt. part of o-nitrobenzenesulphenylalanine and 0.105 wt. part of dicyclohexylcarbodiimide was added to the suspension and the mixture was stirred at 25° C for 30 minutes. The gel was filtered, washed with dichloromethane, dried in vacuum over $P_2O_5$ and analyzed for the content of bound aminoacids.

Splitting of the peptide from the polymeric carrier was carried out by hydrogen bromide in trifluoroacetic acid. The peptidyl copolymer (0.2 wt. part) was mixed into 3 wt. parts of anhydrous trifluoroacetic acid and dry gaseous hydrogen bromide was led in at 0° C for 1 hr. After evaporation, the split product was washed from the carrier with 20 ml of water and refined by chromatography.

EXAMPLE 2

The synthesis was carried out similarly as in Example 1, with the distinction that 0.175 wt. part of tert-butyloxycarbonyl-glycine was used for bonding instead of o-nitrobenzene-sulphenylglycine. After hydrolysis, 0.24 mmole of glycine was found in 1 g of the copolymer by analysis of aminoacids. Tert-butyloxycarbonyglycyl copolymer (0.5 wt. part) was suspended in 5 wt. parts of trifluoroacetic acid and allowed to stand at the room temperature for 30 min. The polymer was filtered off and then washed with dichloromethane until all of the trifluoroacetic acid was washed out.

EXAMPLE 3

The synthesis was carried out analogously as in Example 1, with the distinction that N-hydroxysuccinimide method was used instead of the carbodiimide method to bind further aminoacid. N-Hydroxysuccinimide ester of o-nitrobenzenesulphenylalanine (0.17 wt. part) was added into a suspension of 1 wt. part of glycyl copolymer in 10 wt. parts of dichloromethane and the reaction mixture was stirred for 1 hour at the laboratory temperature. The polymer with linked protected dipeptide was isolated by filtration, washed three times with 20 wt. parts of dichloromethane on the filter, sucked off and dried in vacuum over $P_2O_5$ and NaOH.

EXAMPLE 4

The synthesis was carried out analogously as in Example 1, with the distinction that liquid hydrogen fluoride was used for splitting the peptide from the polymeric carrier. Hydrogen fluoride was distilled in a Daiflon apparatus to 0.2 wt. part of peptidyl copolymer and the suspension was stirred at 0° C for 30 min. Hydrogen fluoride was removed by distillation and the product was washed out from the carrier with 20 wt. parts of water and refined similarly as in Example 1.

EXAMPLE 5

The synthesis was carried out analogously as in Example 1, with the distinction that peptide in the amide form was split off from the polymeric carrier by methanolic ammonia. The peptidyl copolymer (0.2 wt. part) was suspended in 10 wt. parts of methanol, which was previously saturated with gaseous ammonia at 0° C, and the suspension was allowed to stand for 48 hours at 25° C being stirred occasionally. Peptide amide with protected aminogroup was obtained in the filtrate after filtration and washing with methanol and was further worked out according to the type of its protecting group.

EXAMPLE 6

The synthesis was carried out similarly as in Example 1, with the distinction that peptide in the amide form was split off from the polymeric carrier by liquid ammonia. Dry ammonia (10 wt. parts) was distilled to 0.2 wt. part. of the peptidyl copolymer in a steel autoclave. The mixture was heated to the laboratory temperature and allowed to stand for 44 hours. The autoclave was then cooled to −40° C again, opened, ammonia was evaporated and the product was obtained by extraction with methanol.

EXAMPLE 7

The synthesis was carried out analogously as in Example 3, with the distinction that a macroporous copolymer of 2-hydroxyethyl methacrylate (50%), ethylene dimethacrylate (40%) and styrene (10%) was used as the primary carrier.

EXAMPLE 8

The carrier was synthesized analogously as in Example 1, with the distinction that 40 wt. parts of 2-hydroxyethyl acrylate and 40 wt. parts of ethylene diacrylate together with 20 wt. parts of phenyl acrylate were used in copolymerization.

EXAMPLE 9

The carrier was synthesized similarly as in Example 3 with the distinction that methacrylamide, methylene-bis-acrylamide and phenoxyethyl methacrylate were used as monomers.

EXAMPLE 10

The carrier was prepared similarly as in Example 9, with the distinction that acrylamide was used instead of methacrylamide.

EXAMPLE 11

The polymeric carrier was prepared by copolymerization of 2-aminoethyl methacrylate with methylene-bis-acrylamide and phenoxyalkyl methacrylate.

EXAMPLE 12

The carrier was synthesized analogously as in Example 11, with the distinction that aminoethyl acrylate was used instead of aminoethyl methacrylate.

EXAMPLE 13

The carrier was prepared analogously as in Example 9, with the distinction that N-methylmethacrylamide, tetraethylene glycol dimethacrylate and acrylanilide were used as monomers.

EXAMPLE 14

The carrier was synthesized similarly as in Example 1 with the distinction that methacroylated pentaerythritol was used as the crosslinking monomer.

EXAMPLE 15

The carrier was synthesized analogously as in Example 14, with the distinction that divinylbenzene was used as the crosslinking monomer.

EXAMPLE 16

The polymeric carrier was prepared by copolymerization of 60 wt. parts of 2-hydroxyethyl methacrylate with 40 wt. parts of ethylene dimethacrylate. The copolymer was washed and thoroughly dried and then its free hydroxyl groups were condensed with benzoyl chloride — 10 wt. parts of the copolymer was treated with 25 wt. parts of benzoyl chloride. The benzoylated copolymer was washed, dried, and then activated by chloromethylation.

EXAMPLE 17

The polymeric carrier from Example 16 (10 wt. parts) was treated with 5 wt. parts of phenylisocyanate in 20 wt. parts of benzene at 40° C. The reaction product was washed, dried, and activated by chloromethylation.

EXAMPLE 18

The polymeric carrier according to Example 16 was treated with diphenyldichlorosilane in benzene solution at 40° C. The weight ratio of reacting components was analogous as in Example 17. The washed and dried copolymer was activated by chloromethylation.

EXAMPLE 19

The copolymer of 2-hydroxyethyl methacrylate with ethylene dimethacrylate was prepared analogously as in Example 16. p-Acetaminophenoxyethyl methacrylate (5 wt. parts) was used as the third monomer. The copolymer was hydrolyzed in 1% aqueous NaOH at 100° C, washed, and diazotized by treatment with 0.1 N NaNO$_2$ and 0.1 N HCl solution. The resulting diazotized gel was coupled with 10 wt. parts of β-naphthol and then activated by chloromethylation similarly as in Example 1.

We claim:

1. An acrylic polymer having a macroporous structure and suitable for use as a carrier in the controlled synthesis of polypeptides, which comprises the condensation product of (1) the reaction product of (a) a monomer selected from the group consisting of hydroxyalkyl acrylates and hydroxyalkyl methacrylates, and (b) a monomer selected from the group consisting of alkylene diacrylates, alkylene dimethacrylates, polyacrylates and polymethacrylates of polyalcohols, alkylene bisacrylamides, and divinylbenzene; and (2) an aromatic ring-containing compound selected from the group consisting of aromatic acids and their anhydrides and chlorides, aromatic isocyanates, halogenophenylsilanes, and aromatic epoxy compounds, the aromatic ring moiety being chloromethylated.

* * * * *